US012734195B2

(12) United States Patent
Chang et al.

(10) Patent No.: US 12,734,195 B2
(45) Date of Patent: Sep. 15, 2026

(54) COMPOSITION FOR TREATING INFECTIOUS DISEASES, COMPRISING EXOSOMES DERIVED FROM THROMBIN-TREATED STEM CELLS

(71) Applicant: SAMSUNG LIFE PUBLIC WELFARE FOUNDATION, Seoul (KR)

(72) Inventors: Yun Sil Chang, Seoul (KR); Won Soon Park, Seoul (KR); So Yoon Ahn, Gyeonggi-do (KR); Dong Kyung Sung, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 447 days.

(21) Appl. No.: 18/036,474

(22) PCT Filed: Nov. 23, 2021

(86) PCT No.: PCT/KR2021/017272
§ 371 (c)(1),
(2) Date: May 11, 2023

(87) PCT Pub. No.: WO2022/114730
PCT Pub. Date: Jun. 2, 2022

(65) Prior Publication Data

US 2023/0405050 A1 Dec. 21, 2023

(30) Foreign Application Priority Data

Nov. 26, 2020 (KR) ........................ 10-2020-0161582
Nov. 22, 2021 (KR) ........................ 10-2021-0161294

(51) Int. Cl.
*A61K 35/50* (2015.01)
*A61K 35/28* (2015.01)
*A61K 45/06* (2006.01)
*A61P 11/00* (2006.01)
*A61P 37/06* (2006.01)
*C12N 5/0775* (2010.01)

(52) U.S. Cl.
CPC .............. *A61K 35/28* (2013.01); *A61K 35/50* (2013.01); *A61K 45/06* (2013.01); *A61P 37/06* (2018.01); *C12N 5/0668* (2013.01)

(58) Field of Classification Search
CPC ........ A61K 35/50; C12N 5/0668; A61P 11/00
See application file for complete search history.

(56) References Cited

U.S. PATENT DOCUMENTS 10,723,997 B2 7/2020 Chang et al.
2014/0065240 A1 3/2014 Mitsialis et al.
2017/0087187 A1 3/2017 Chang et al.
2018/0100149 A1* 4/2018 Marbán .................. A61P 43/00
2019/0314469 A1 10/2019 Chang et al.

FOREIGN PATENT DOCUMENTS

EP 4137140 A1 2/2023
EP 4181935 A1 5/2023
JP 2017521357 A 8/2017
JP 2020527361 A 9/2020
KR 10-1661847 B1 9/2016
KR 10-2017-0119019 A 10/2017
KR 10-2018-0003999 A 1/2018

OTHER PUBLICATIONS

Lin et al. Gene Therapy for ALI/ARDS. Crit Care Clin. 2011;27(3):705-718.*

Morrison et al., “Mesenchymal Stromal Cells Modulate Macrophages in Clinically Relevant Lung Injury Models by Extracellular Vesicle Mitochondrial Transfer,” Am J Respir Crit Care Med., 2017, vol. 196 Iss. 10, p. 1275-1286.

Sengupta Vikram et al., “Exosomes Derived 1-12 from Bone Marrow Mesenchymal Stern Gells as Treatment for Severe COVID-19”, Stem Gells and Development, vol. 29, No. 12, May 12, 2020.

Akbari Ali et al., “Potential therapeutic 1-12 application of mesenchymal stem cell-derived exosomes in SARS-CoV-2 pneumonia”, Stem Cell Research & Therapy, vol. 11, No. 1, Aug. 14, 2020.

Office Action from corresponding Japanese Application No. 2023-528342, dated Apr. 23, 2024.

Extended European Search Report from corresponding European Application No. 21898556.2, dated May 7, 2024.

Qian. Xiao1i et al., “Immunosuppressive effects of mesenchymal stem cells-derived exosomes.”, Stem Cell Reviews and Reports. Sep. 15, 2020 (on1ine). <DOI: https://doi.org/1O.1007/s12015-020-10040-7>.

International Search Report from corresponding PCT Application No. PCT/KR2021/017272, dated Jun. 30, 2022.

* cited by examiner

*Primary Examiner* — Lynn Y Fan
(74) *Attorney, Agent, or Firm* — Harness, Dickey & Pierce, P.L.C.

(57) ABSTRACT

The present invention relates to: a pharmaceutical composition for preventing or treating infectious diseases, comprising, as an active ingredient, exosomes derived from thrombin-treated stem cells; a pharmaceutical formulation containing same; and a preparation method therefor. The present inventors specifically have identified that exosomes isolated from thrombin-treated stem cells significantly reduce the expression of inflammatory cytokines under inflammatory conditions, and thus it is expected that the exosomes derived from thrombin-treated stem cells, according to the present invention, can be effectively used in related fields for the purpose of alleviating or treating various infectious diseases caused by immune responses or inflammatory responses induced through infection.

2 Claims, 2 Drawing Sheets

TNF-a 800
600
400
200
0
(pg/ml)
*
ARDS
ARDS-exo

COMPOSITION FOR TREATING INFECTIOUS DISEASES, COMPRISING EXOSOMES DERIVED FROM THROMBIN-TREATED STEM CELLS

CROSS-REFERENCE TO RELATED APPLICATIONS

This application is a national phase application of PCT Application No. PCT/KR2021/017272, filed on 23 Nov. 2021, which claims benefit of Korean Patent Application Nos. 10-2020-0161582, filed on 26 Nov. 2020 and 10-2021-0161294, filed on 22 Nov. 2021. The entire disclosure of the applications identified in this paragraph are incorporated herein by references.

TECHNICAL FIELD

The present invention relates to a pharmaceutical composition for preventing or treating an infectious disease, including an exosome derived from a thrombin-treated stem cell, a pharmaceutical preparation containing the same, and a method of preparing the same.

BACKGROUND

Infectious diseases are diseases caused by infection by microbes such as bacteria, viruses, fungi and protozoa, or parasites, and classified into various diseases according to the type of microbe responsible for the infection. Microbial infections may affect a part (local infection) or all (systemic infection) of the body, with local infections including, for example, abscesses and bladder infections, and severe systemic infections including sepsis and septic shock. Symptoms caused by infections may include fever, a rapid pulse, shortness of breath, anxiety, and confusion, and in most cases, the effects of infection resolve when the infection is effectively treated.

Acute Respiratory Distress syndrome (ARDS), of which a severe infection such as sepsis is one of the main causes, developed due to severe inflammation in the lungs when a substance such as a cytokine is secreted into the blood due to an infection or body injury and reaches the lungs. Research results have been reported that various inflammatory cytokines are involved in initiating and amplifying inflammatory responses in ARDS, and it is known that the balance between an inflammatory mediator and an anti-inflammatory mediator also plays an important role (Korean Journal of Internal Medicine, vol. 68 (5); total vol. 537, 2005). In this disease, symptoms of severe respiratory distress to the extent that life cannot be maintained without a ventilator usually appear several hours to several days after exposure to the causative factor. Generally, for treatment, intensive care with mechanical ventilation using a ventilator is executed, which is not a fundamental treatment but supports the breathing of the patient for the time so that the patient's lungs can heal. While various attempts have been made to reduce patient mortality, currently, mechanical ventilation is almost the only method. Moreover, when this disease is accompanied by an infection, antibiotic treatment is also executed. However, it is an intractable disease for which there are still few effective therapies, and thus it is urgent to develop a therapeutic agent for the disease.

On the other hand, stem cells are known as cells involved in the regeneration, treatment and immune responses of tissue as well as being multipotent, and using these characteristics, efforts have been made to develop therapeutic agents for various diseases and symptoms using mesenchymal stem cells that have been separated from umbilical cord blood, bone marrow and the like and cultured. However, a cell therapy using stem cells alone has limitations such as the possibility of tumorigenicity due to DNA transfer, the possibility of vascular obstruction or myocardial infarction caused by their large size, rejection caused by a cell surface antigen during allogeneic transplantation, a difficult manufacturing process, and high production costs.

Exosomes are small vesicles (diameter: approximately 30 to 100 nm) with a membrane structure, secreted from various cells, and according to research using electron microscopy, it has been observed that exosomes are not directly detached from the plasma membrane, but originate from specific compartments in cells, called multivesicular bodies (MVBs), and are released or secreted from the cells. That is, when fusion of the polycystic body and the plasma membrane has occurred, small vesicles called exosomes are released into an external environment. Although the specific molecular mechanism that makes these exosomes has not been identified, it is known that not only red blood cells, but also various types of immune cells including B lymphocytes, T lymphocytes, dendritic cells, platelets and macrophages, as well as tumor cells and stem cells also produce and secrete exosomes in a living state.

Particularly, exosomes derived from stem cells are known to play a role in cell-to-cell communication because they contain receptors and proteins as well as nuclear components. In addition, because exosomes derived from stem cells contain relatively smaller amounts of animal serum than stem cells, the risk of zoonosis due to animal serum infection may also be excluded. Considering these characteristics of exosomes, a cell therapy using exosomes is expected to be a new paradigm that can overcome the limitations of existing stem cell therapies.

DISCLOSURE

Technical Problems

As a result of research efforts by applying exosomes derived from stem cells to infectious diseases, the present inventors confirmed that a group treated with thrombin-treated, stem cell-derived exosomes exhibits an excellent anti-inflammatory effect due to a decrease in production of inflammatory cytokines by creating an infectious environment by treating Raw 264.7 cells with a lipid polysaccharide (LPS) and treating the cells with stem cell-derived exosomes treated with each of thrombin, LPS, and TNF, and based on this finding, completed the present invention.

Therefore, the present invention is directed to providing a pharmaceutical composition for preventing or treating an infectious disease, including thrombin-treated stem cell-derived exosomes as an active ingredient.

In addition, the present invention is directed to providing a pharmaceutical preparation for treating an infectious disease, including the pharmaceutical composition.

In addition, the present invention is directed to providing a method of preparing the pharmaceutical composition.

However, technical problems to be solved in the present invention are not limited to the above-described problems, and other problems which are not described herein will be fully understood by those of ordinary skill in the art from the following descriptions.

Technical Solutions

To achieve the purpose of the present invention, the present invention provides a pharmaceutical composition for preventing or treating an infectious disease, including thrombin-treated stem cell-derived exosomes as an active ingredient.

In one embodiment of the present invention, the stem cells may be selected from the group consisting of mesenchymal stem cells, human tissue-derived mesenchymal stromal cells, human tissue-derived mesenchymal stem cells, multipotent stem cells, and amniotic epithelial cells.

In another embodiment of the present invention, the mesenchymal stem cells may be derived from an umbilical cord, umbilical cord blood, bone marrow, fat, muscle, skin, an amnion, a placenta, or other tissues.

In still another embodiment of the present invention, the infectious disease may be selected from the group consisting of an infectious lung disease, sepsis, and systemic inflammatory response syndrome.

In yet another embodiment of the present invention, the infectious lung disease may be acute respiratory distress syndrome (ARDS).

In yet another embodiment of the present invention, the pharmaceutical composition may further include an auxiliary ingredient selected from the group consisting of a culture medium, a cytokine, and a gene.

In addition, the present invention provides a pharmaceutical preparation for treating an infectious disease, including the pharmaceutical composition.

In one embodiment of the present invention, the pharmaceutical preparation may be formulated in the form of an injection, infusion, spray, liquid, or patch.

In addition, the present invention provides a method of preparing the pharmaceutical composition, including the following steps:

(a) culturing stem cells and treating the stem cells with thrombin;

(b) isolating exosomes from the culture fluid obtained in (a); and (c) preparing a composition containing the exosomes isolated in (b) as an active ingredient.

In one embodiment of the present invention, the thrombin of (a) may be included in the medium at 1 to 1,000 unit/ml.

In another embodiment of the present invention, the exosomes of (b) may be isolated by centrifugation at 3,000 to 100,000 g for 10 minutes to 5 hours.

In addition, the present invention provides a method of preventing or treating an infectious disease, including administering the pharmaceutical composition into a subject.

In addition, the present invention provides a use of the pharmaceutical composition to prevent or treat an infectious disease.

Advantageous Effects

The present inventors confirmed concretely that the expression of inflammatory cytokines is significantly reduced under the condition of the induction of inflammation in exosomes isolated from thrombin-treated stem cells as compared to those not treated with thrombin or treated with another substance, and thus the thrombin-treated stem cell-derived exosome according to the present invention is expected to be effectively used in fields associated with improving or treating various infectious diseases through immune responses or inflammatory responses induced by infections.

MODES OF THE INVENTION

Figure 1:
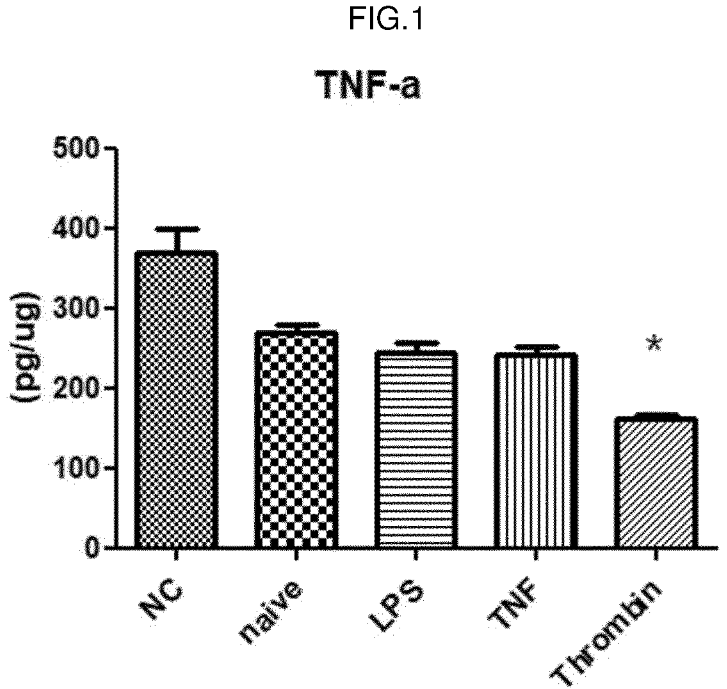
FIG. 1 shows the result of treating RAW 264.7 cells with LPS, treating the cells with exosomes isolated from stem cells treated with exosomes (naive) isolated from untreated stem cells, and exosomes isolated from stem cells treated with each of LPS, TNF and thrombin, and then measuring the concentrations of inflammatory cytokines TNF-α and IL-1β in the cell culture fluids.
Figure 1:
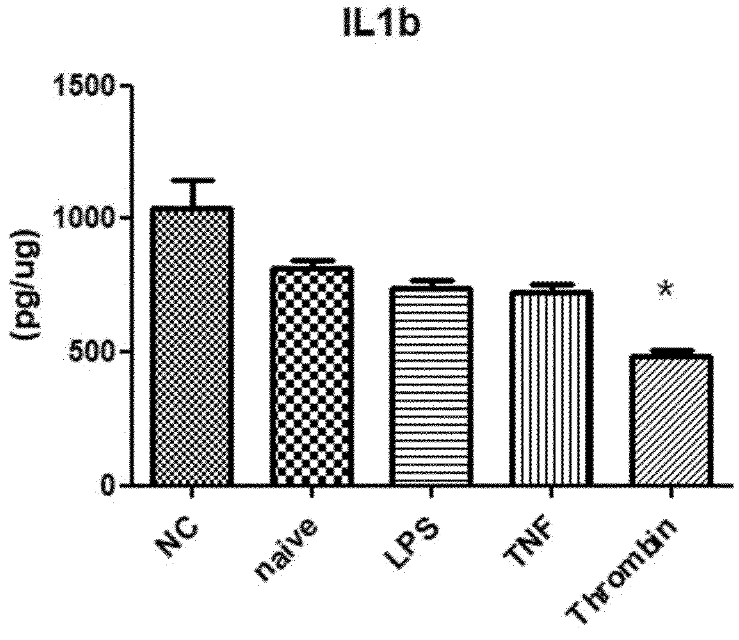

The present inventors confirmed an excellent anti-inflammatory effect of thrombin-treated stem cell-derived exosomes in an infectious environment, and based on this, completed the present invention.

Therefore, the present invention provides a pharmaceutical composition for preventing or treating an infectious disease, including thrombin-treated stem cell-derived exosomes as an active ingredient.

The term "thrombin" used herein refers to a protease involved in blood coagulation, serving to catalyze a reaction of hydrolyzing soluble fibrinogen in blood and changing the hydrolyzed fibrinogen into insoluble fibrin. In the present invention, when stem cells are treated with thrombin, the thrombin effectively improves the infectious disease treating effect of the exosomes isolated from the stem cells.

The term "stem cell" used herein refers to an undifferentiated cell which has differentiation potency but has not differentiated yet, and a cell having self-replicability and the ability to differentiate into two or more different types of cells. The stem cells of the present invention may be autologous or homologous stem cells, and may be derived from any type of animal, including humans and non-human mammals.

In the present invention, the stem cells of the present invention include embryonic stem cells or adult stem cells, and preferably adult stem cells. The adult stem cells may be mesenchymal stem cells, human tissue-derived mesenchymal stromal cells, human tissue-derived mesenchymal stem cells, or multipotent stem cells, and preferably mesenchymal stem cells, but the present invention is not limited thereto.

The mesenchymal stem cells may be mesenchymal stem cells derived from an umbilical cord, umbilical cord blood, bone marrow, fat, muscle, skin, an amnion, a placenta, or other tissues, but the present invention is not limited thereto.

The term "exosome" used herein refers to a small vesicle (diameter: approximately 30 to 100 nm) with a membrane structure, secreted from various cells, and a small vesicle released to an extracellular environment when MVBs are fused with the plasma membrane. The exosomes are naturally secreted, or artificially secreted. Since an exosome-based therapeutic agent is a cell-free preparation, it does not include DNA and thus has a low risk of oncogenesis. Such an exosome-based therapeutic agent is safe because it has no cell surface antigen and no problem of rejection. In addition, since the exosome-based therapeutic agent is an isolated material, it allows drugs to be developed as off-the-shelf products and thus reduces production costs.

The term "prevention" used herein refers to all actions of inhibiting infectious diseases or delaying the onset thereof by the administration of the pharmaceutical composition according to the present invention.

The term "treatment" used herein refers to all actions involved in alleviating or beneficially changing symptoms of infectious diseases by the administration of the pharmaceutical composition according to the present invention.

The term "infectious disease" used herein includes all diseases caused by microbes such as bacteria, viruses, fungi and protozoa, or parasites, preferably diseases caused by immune responses and inflammatory responses induced by infections, which more preferably may be selected from the group consisting of infectious lung diseases, sepsis and systemic inflammatory response syndrome, and infectious lung diseases, most preferably ARDS.

ARDS is an intractable disease with few therapeutic methods and may mainly develop from a severe infection or pneumonia, or from a physical injury or other organ problems. Due to ARDS, a blood oxygen level may decrease and damaged lung cells and specific cytokines secreted by white blood cells may leak into the bloodstream, causing inflammation and complications in other organs.

Sepsis is a systemic response to a microbial infection, and it is known that high frequencies of several species of bacteria, particularly, gram negative bacteria such as *E. coli, Pseudomonas aeruginosa, Klebsiella pneumoniae*, etc., is a cause of sepsis/septic shock. Pathophysiologically, the entire immune system, including various blood cells and endothelial cells as well as bone marrow, is activated to remove infectious bacteria that invade from outside the body, and it is reported that the major organs are damaged by various mediators such as cytokines secreted during this process.

Systemic inflammatory response syndrome is a clinical condition in which two or more of fever, a low body temperature, a rapid pulse, shortness of breath and an abnormally high level of white blood cells among symptoms caused by inflammation are present simultaneously.

The pharmaceutical composition of the present invention may further include an auxiliary ingredient selected from the group consisting of a culture medium, a cytokine, and a gene.

The pharmaceutical composition of the present invention may be used alone, or in combination with methods using different therapeutic agents to treat infectious diseases.

The pharmaceutical composition of the present invention may include exosomes derived from thrombin-treated stem cells, and further include a pharmaceutically acceptable carrier. The pharmaceutically acceptable carrier is generally used in formulations, and examples of such carriers include saline, distilled water, Ringer's solution, buffered saline, cyclodextrin, a dextrose solution, a maltodextrin solution, glycerol, ethanol, liposomes, etc., but the present invention is not limited thereto. If needed, the pharmaceutically composition may further include other conventional additives including an antioxidant, a buffer, etc. In addition, by additionally adding a diluent, a dispersant, a surfactant, a binder or a lubricant, the pharmaceutical composition may be formulated in an injectable form such as an aqueous solution, an emulsion or a suspension, a pill, a capsule, a granule, or a tablet. Suitable pharmaceutically acceptable carriers and their formulations may be formulated according to each ingredient using a method disclosed in Remington's Pharmaceutical Science.

The pharmaceutical composition of the present invention may be administered orally or parenterally (e.g., intravenously, subcutaneously, intraperitoneally, intratracheally, endobronchially, or locally) according to a desired method, and a dose of the pharmaceutical composition of the present invention may be selected according to a patient's condition and body weight, severity of a disease, a dosage form, an administration route and duration by those of ordinary skill in the art.

The pharmaceutical composition of the present invention is administered at a pharmaceutically effective amount. The term "pharmaceutically effective amount" used herein refers to an amount sufficient for treating a disease at a reasonable benefit/risk ratio applicable for medical treatment, and an effective dosage may be determined by parameters including the type and severity of a patient's disease, drug activity, sensitivity to a drug, administration time, an administration route and an excretion rate, the duration of treatment and drugs simultaneously used, and other parameters well known in the medical field. The pharmaceutical composition according to the present invention may be administered separately or in combination with other therapeutic agents, and may be sequentially or simultaneously administered with a conventional therapeutic agent, or administered in a single or multiple dose(s). In consideration of all of the above-mentioned parameters, it is important to achieve the maximum effect with the minimum dose without side effects, and such a dose may be easily determined by one of ordinary skill in the art.

Specifically, the effective amount of the pharmaceutical composition of the present invention may be changed according to a patient's age, sex, condition, and weight, the absorption of an active ingredient in the body, an inactivation rate, an excretion rate, a disease type, or a co-administered drug. The pharmaceutical composition of the present invention may generally be administered at 0.001 to 150 mg, and preferably 0.01 to 100 mg per kg of body weight daily or every other day, or administered in divided doses once to three times a day. However, since the dose may be increased or decreased depending on an administration route, the severity of obesity, sex, a body weight or age, the above-mentioned dose does not limit the scope of the present invention in any way.

In addition, the present invention provides a pharmaceutical preparation for treating an infectious disease, including the pharmaceutical composition.

The pharmaceutical preparation may be formulated in the form of an injection, infusion, spray, liquid, or patch, but the present invention is not limited thereto. A suitable form for treating a corresponding infectious disease may be selected and used by one of ordinary skill in the art.

In the present invention, according to exemplary embodiments, it was confirmed that exosomes derived from thrombin-treated stem cells have an excellent therapeutic effect on an infectious disease.

In one embodiment of the present invention, cord blood-derived mesenchymal stem cells were treated with thrombin and cultured, and exosomes were isolated through centrifugation (refer to Example 1).

In another embodiment of the present invention, to evaluate the therapeutic effect of the exosomes on infectious diseases, Raw 264.7 cells, which are mouse-derived macrophages, were treated with LPS, and then treated with exosomes isolated from untreated stem cells, or exosomes isolated from stem cells treated with each of LPS, TNF and thrombin, and the concentrations of the inflammatory cytokines TNF-$\alpha$ and IL-1$\beta$ in a cell culture fluid were measured, whereby it was confirmed that the concentrations of both cytokines were significantly reduced only in the group treated with thrombin-treated stem cell-derived exosomes (refer to Example 2-1).

In addition, also in the case of infectious disease animal models, compared with a control (saline-administered group), it can be seen that, in the group treated with thrombin-treated stem cell-derived exosomes (ARDS-exo), the concentrations of inflammatory cytokines such as TNF-α, IL-1β, and IL-6 are statistically significantly reduced (refer to Example 2-2).

Therefore, in another aspect of the present invention, the present invention provides a method of preparing the pharmaceutical composition, which includes: (a) culturing stem cells and treating the cells with thrombin; (b) isolating exosomes from the culture fluid of (a); and (c) preparing a composition containing the exosomes isolated in (b) as an active ingredient.

In the present invention, the concentration of the treated thrombin is not particularly limited as long as it is any condition suitable for enhancing the efficiency of stem cells/exosomes, and the thrombin is preferably included in a medium at 1 to 1,000 units/ml.

In the present invention, the method of isolating exosomes is not limited, and exosomes may be isolated from the culture fluid using, for example, centrifugation, ultra-high-speed centrifugation, filtration using a filter, gel filtration chromatography, free-flow electrophoresis, capillary electrophoresis, isolation using a polymer, and a combination thereof, and preferably centrifugation/ultra-high-speed centrifugation. Here, the centrifugation/ultra-high-speed centrifugation is preferably performed at 4° C. and 3,000 to 100,000 g for 10 minutes to 5 hours.

A medium used for cell culture in the present invention is a mixture for the growth and proliferation of cells such as stem cells in vitro, including an element required for cell growth and proliferation, such as sugars, amino acids, various nutrients, serums, growth factors, and minerals. The medium that can be used in the present invention may be a commercially manufactured medium such as a Dulbecco's modified Eagle's medium (DMEM), a minimal essential medium (MEM), a basal medium eagle (BME), RPMI1640, a Dulbecco's modified Eagle's medium: nutrient mixture F-10 (DMEM/F-10), a Dulbecco's modified Eagle's medium: nutrient mixture F-12 (DMEM/F-12), an α-minimal essential medium (α-MEM), a Glasgow's minimal essential medium (G-MEM), an Isocove's modified Dulbecco's medium (IMDM), or a knock-out DMEM, or an artificially synthesized medium, but the present invention is not limited thereto.

In still another aspect of the present invention, the present invention provides a method of preventing or treating an infectious disease, which includes administering a pharmaceutical composition including exosomes derived from thrombin-treated stem cells as an active ingredient to a subject.

The term "subject" used herein refers to a target in need of treatment, and more specifically, a mammal such as a human or a non-human primate, a mouse, a rat, a dog, a cat, a horse, or a cow.

In addition, the present invention provides a use of the pharmaceutical composition for preventing or treating an infectious disease.

Hereinafter, to facilitate understanding of the present invention, exemplary examples will be suggested. However, the following examples are merely provided so that the present invention can be more easily understood, and not to limit the present invention.

EXAMPLES

Example 1. Induction to Secrete Exosomes by Treatment of Stem Cells With Thrombin Human cord blood-derived mesenchymal stem cells ($3\times10^5$) were seeded in a 100 mm culture plate (orange scientific cat #4450200) and cultured for 1 week. After it was confirmed that the cells were saturated in the culture plate, the medium was exchanged with a serum-free culture medium (MEM alpha media) in which 50 units/ml thrombin (REYON Pharmaceutical. Co., Ltd.) was diluted, followed by culturing again for 6 hours. Afterward, the culture fluid was divided into centrifuge tubes and centrifuged at 4° C. and 6,000 rpm for 30 minutes, the supernatant was transferred to a new tube to remove cell debris. Again, the supernatant was ultracentrifuged at 4° C. and 100,000 rpm for 2 to 4 hours, and then a resulting supernatant was further removed, thereby obtaining exosomes.

Example 2. Confirmation of Anti-Inflammatory and Anti-Infectious Effects Due to Exosomes Derived From Thrombin-Treated Stem Cells The present inventors conducted the following experiments to see whether thrombin-treated stem cell-derived exosomes could treat diseases induced by infections such as ARDS according to the anti-inflammatory effect.

2-1. In Vitro Experiment

After culturing RAW 264.7 cells, which are mouse-derived macrophages, the cells were activated by treatment with a lipopolysaccharide (LPS) present in the membrane of a gram-negative bacterium, which is an external immune inducer. Subsequently, after treatment with exosomes isolated from untreated stem cells, or exosomes isolated from LPS, TNF, or thrombin-treated stem cells, the concentrations of representative inflammation-inducing cytokines, tumor necrosis factor-α (TNF-α) and interleukin 1 beta (IL-1β), in the culture medium were measured.

As a result, as confirmed in FIG. 1, in a control (NC) in which RAW 264.7 cells were treated with LPS alone, it was seen that the concentrations of TNF-α and IL-1β in a culture medium were increased. On the other hand, in a group (naive) treated with exosomes derived from untreated stem cells, and a group treated with exosomes derived from LPS or TNF-treated stem cells, compared with the control, the concentrations of the cytokines in each culture fluid were reduced. In addition, particularly in the case of exosomes derived from thrombin-treated stem cells, it was confirmed that the production amounts of both cytokines were statistically significantly reduced.

2-2. In Vivo Experiment (Infectious Disease Animal Model)

To manufacture an infectious disease animal model (ARDS mouse model), a mouse (aged 16 to 24 weeks) was anesthetized by intraperitoneal administration of diluted Rompun and Ketamine saline, a catheter was intubated into its airway, and 0.05 cc of *E. coli* was administered endotracheally using a 1 ml syringe.

After *E. coli* administration, each of a saline-administered group (ARDS) and a group administered with exosomes derived from thrombin-treated stem cells (ARDS-exo) was divided into two groups, which were administered with saline and exosomes. After 24 hours, the mice were sacrificed by respiratory anesthesia using an Ipran solution, each mouse was incised to show the airway at its neck, and a catheter was intubated endotracheally and then fixed with sutures. Saline was injected into the lungs using a syringe, and a bronchoalveolar lavage (BAL) fluid was collected carefully from the lungs. The collected BAL fluid was kept frozen at −70° C. before a supernatant from which the cells and bacteria were removed was biochemically accessed through centrifugation.

The BAL fluid that had been stored at −70° C. was slowly melted at 4° C., and the concentration of inflammatory cytokines (TNF-α, IL-1β, and IL-6) was measured using a multiplex cytokine kit according to a manufacturer's protocol.

Figure 2:
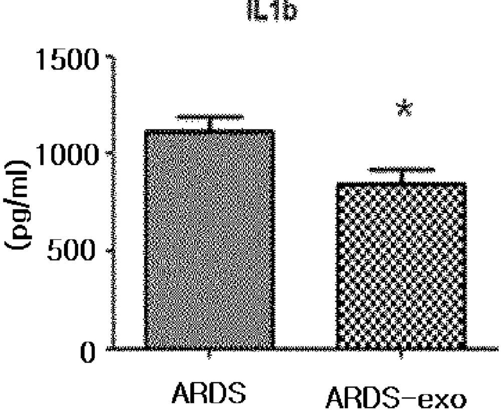
FIG. 2 shows the result of measuring the concentrations of inflammatory cytokines (TNF-α, IL-1β, and IL-6) of a saline-administered group (control, ARDS) and a thrombin-treated stem cell-derived exosome-administered group (ARDS-exo) in infectious disease animal models.
Figure 2:
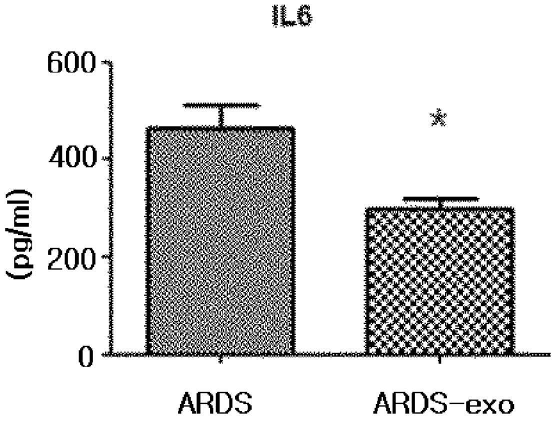

As a result, it can be seen from FIG. 2 that, in the case of infectious disease mouse models, the concentrations of inflammatory cytokines such as TNF-α, IL-1β, and IL-6 are statistically significantly (t-test) reduced in the exosome-administered group (ARDS-exo), compared with the saline-administered group (ARDS).

The above result reveals that exosomes derived from thrombin-treated stem cells have excellent anti-inflammatory and infectious disease treating effects, demonstrating that the exosomes can be used in treatment of various diseases caused by inflammations induced by immune responses due to the anti-inflammatory effect, particularly infectious diseases.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

What is claimed is:

1. A method for treating acute respiratory distress syndrome (ARDS), the method comprising:

administering an effective amount of a pharmaceutical composition comprising exosomes derived from thrombin-treated stem cells as an active ingredient to an individual in need thereof, wherein the stem cells are mesenchymal stem cells derived from an umbilical cord.

2. The method of claim 1, wherein the pharmaceutical composition further comprises a culture medium, a cytokine, or a gene.

* * * * *